United States Patent [19]

Van Ewijk

[11] 4,265,902
[45] May 5, 1981

[54] THERAPEUTIC TREATMENT OF HORSES

[75] Inventor: William Van Ewijk, Haarlem, Netherlands

[73] Assignee: Tetra Consultants, Inc., New Rochelle, N.Y.

[21] Appl. No.: 136,903

[22] Filed: Apr. 3, 1980

[51] Int. Cl.$^3$ ............................................. A61K 31/415
[52] U.S. Cl. ................................................. 424/273 R
[58] Field of Search .................................... 424/273 R

[56] References Cited

U.S. PATENT DOCUMENTS 3,830,908  8/1974  Klippel et al. ...................... 424/28

Primary Examiner—Sam Rosen

[57] ABSTRACT

Therapeutically treating horses suffering from tail and mane eczema by systemically administering to said horses a small but effective amount of allantoin.

5 Claims, No Drawings

THERAPEUTIC TREATMENT OF HORSES

This invention relates to a method of therapeutically treating horses suffering from tail and mane eczema. Tail and mane eczema is a disease of horses, including ponies, which manifests itself as a dermatitis like disease at the root of the hair of the horses tail and mane and is accompanied by extreme itching and pain as well as substantial loss of hair at the base of the tail or the mane of the afflicted animal. Tail and mane eczema has been known by other names, for example, in Australia it is sometimes known as "The Queensland Itch" and in Great Britian it occasionally is identified as "The Sweet Itch".

This disease is most prevalent in the stricken animals during the summer season especially when it is hot and humid, and once an animal is sensitive to the disease, i.e., susceptible and contracts the disease, the symptoms occur each summer season, regardless of the age of the animal. Tail and mane disease, while not a debilitating or life threatening disease, does have serious economic consequences as well as adverse physiological effects in the animal suffering from the disease. The commercial value of any animal stricken with the disease is adversely affected, especially when the symptomology is severe enough to cause the loss of hair which is incident to the disease.

Although the exact nature of this disease is not completely understood, it is known to be either caused or carried by certain species of insects of the class deptera and family culicidae, commonly called mosquitoes. Current theory presently holds that the horse bitten by the mosquito suffers a toxic reaction manifesting itself as tail and mane eczema.

In the past, therapeutic treatment of this disease has only been partially successful, if at all. The most prevalent method of treating the disease has been by prophylactic methods, i.e., keeping the horses and mosquitoes separated. This has lead to prevention programs wherein the horses were stabled in mosquito secure quarters from dusk to dawn, the most prevalent biting time for mosquitoes. Widespread use of insecticides to destroy the mosquitoes has also been employed. Attempts have been made to treat the stricken animals with anti-inflammatory drugs, for example, corticoid steroids, such as triamcinolone acetonide, to counteract the symptoms of the disease. Up to the present, all these attempts to either treat or cure the disease have met with failure and have not completely alleviated the condition of the stricken animal or prevented the recurrence of the disease.

I have now discovered a method to therapeutically treat horses suffering from tail and mane eczema caused by culicidae insects, which comprises systemically administering to the stricken horse a small but effective amount of allantoin. More specifically, I have found that horses suffering from tail and mane eczema may be therapeutically treated and cured of the disease, if a small but effective amount of allantoin is systemically administered to the animal over an extended period of time.

The allantoin which may be employed in the practice of this invention is a compound having the formula,

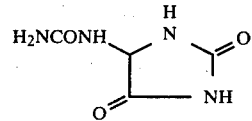

and has been known for many years to be useful in the treatment of dermatological conditions, including the treatment of skin ulcers, burns and flea bites. Reference may be had to the following publications in relation to the foregoing prior art therapeutic uses of allantoin: Merck Index, 9th Edition, page 35; Drug and Cosmetic Journal, January 1959, pp 36 et seq., and U.S. Pat. Nos. 2,761,867 and 4,117,141. I have also found that the therapeutically acceptable salts of allantoin may also be employed in the practice of this invention.

The allantoin compounds useful in the practice of this invention must be systemically administered to the horse suffering from tail and mane eczema. Systemic administration may be accomplished by parenterally or perorally administering the therapeutic amounts of allantoin useful in the practice of this invention. Parenteral administration may be satisfactorily accomplished by subcutaneous, intramuscularly or intravenous injection. Most preferably, subcutaneous or intramuscular injections yield most satisfactory results. Peroral administration may be accomplished in any manner known to the skilled worker, for example, by oral administration of capsules, boluses or liquid formulations, or by mixing the desired amounts of allantoin with the animal's feed to accomplish the required administration of the allantoin compound.

For parenteral administration, allantoin may be administered in aqueous solutions. It has been found that satisfactory results may be obtained in the practice of this invention when a solution containing from about 0.2 to about 5.0 percent by weight of allantoin. Most satisfactory results are obtained when the solution contains from 0.5 to 1.5 percent by weight of allantoin, although other concentrations also provide acceptable results.

It has been found that therapeutically acceptable results may be obtained when the allantoin compounds of this invention are systemcially administered to the horses suffering from tail and mane eczema in a sufficient amount over an extended period of time. I have found that satisfactory results are obtained when the allantoin is systemically administered to the animal at a dosage level of from 0.01 to 10.0 mg/kilogram of the horses' body weight and preferably from 0.01 to 2.0 mg/kilograms of body weight and most preferably from 0.03 to 0.5 mg/kilogram of body weight. It has been found preferable to administer the allantoin compound to the animal being treated on a dosage schedule that involves administration at least once a week for from 6 to 12 weeks and then once each month thereafter until a cure is obtained. However, it is understood by the skilled worker that the dosage amounts and schedule of systemic administration of the allantoin compounds to be employed in accordance with the practice of the instant invention may be varied depending upon the requirements of the horse being treated and the results obtained.

In the event that systemic administration of the allantoin compound requires injection into the bloodstream, a buffered saline solution can be employed. For example, a buffered aqueous saline solution may be prepared employing such salts as NaCl or KCl as well as buffering agents such as $Na_2HPO_4$ or $KH_2PO_4$ to give a pH range of between 5 and 9, as is well known in the art.

The invention may be illustrated by the following Examples.

EXAMPLE 1

A 1.0% solution of allantoin in phosphate buffered saline solution containing 1% sodium alginate was prepared as described below. The following salts in the amounts indicated were dissolved in 125 ml of distilled water.

| Salt | Amount (gm) |
| --- | --- |
| NaCl | 1.0 |
| KCl | 0.025 |
| $Na_2HPO_4$ | 0.176 |
| $KH_2PO_4$ | 0.02 |

To this solution was added 1.25 gm of sodium alginate with stirring until complete dissolution was obtained. There was then added 1.25 gm of allantoin, with stirring until it was completely dissolved. The resultant solution was then filtered and sterilized and placed in a vial and kept under refrigeration until use.

EXAMPLE 2

Ten horses, each weighing about 300 kilograms, and all suffering from tail and mane eczema were treated with the solution obtained in Example 1. The treatment consisted of a series of parenteral injections administered to the animals once each week for a period of 8 weeks; followed by an additional series of injections given once each month for a period of 4 months. The dosage of each of the injections administered to each animal provided 0.3 mg of allantoin per kilogram of weight of the animal being treated. By the end of the series of injections given, all the animals were cured of the tail and mane eczema, all symptomology having disappeared and further treatment was stopped.

The invention may be variously otherwise encompassed within the scope of the appended claims.

What is claimed is:

1. A method of therapeutically treating horses suffering from tail and mane eczema which comprises, systemically administering, over a period of time, to a horse suffering from tail and mane eczema a small but effective amount of allantoin.

2. The method of claim 1 wherein the tail and mane eczema is caused by Culicidae insects.

3. The method of claim 1, wherein the amount of allantoin administered is from about 0.01 to about 10.0 milligrams per kilogram of weight of the horse being treated.

4. The method of claim 1, wherein the systemic administration is accomplished parenterally.

5. The method of claim 1, wherein the systemic administration is accomplished perorally.

* * * * *